(12) United States Patent
Al-Ali

(10) Patent No.: US 6,377,829 B1
(45) Date of Patent: Apr. 23, 2002

(54) RESPOSABLE PULSE OXIMETRY SENSOR

(75) Inventor: Ammar Al-Ali, Tustin, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 09/456,666

(22) Filed: Dec. 9, 1999

(51) Int. Cl.[7] .................................................. A61B 5/00
(52) U.S. Cl. ...................................... 600/323; 600/344
(58) Field of Search ................. 600/309–311, 322–326, 600/344, 315–316; 356/39–41

(56) References Cited

U.S. PATENT DOCUMENTS

| | | | |
|---|---|---|---|
| 4,621,463 A | | 11/1986 | New, Jr. et al. |
| 5,090,410 A | | 2/1992 | Saper et al. |
| 5,158,323 A | | 10/1992 | Yamamoto et al. |
| 5,170,786 A | | 12/1992 | Thomas et al. |
| 5,209,230 A | * | 5/1993 | Swedlow et al. ........... 600/332 |
| 5,638,818 A | | 6/1997 | Diab et al. |
| 5,660,567 A | | 8/1997 | Nierlich et al. |
| 5,678,544 A | * | 10/1997 | DeLonzor et al. .......... 600/344 |
| 5,758,644 A | | 6/1998 | Diab et al. |
| 5,919,133 A | | 7/1999 | Taylor et al. |
| 5,995,855 A | | 11/1999 | Kiani et al. |
| 5,999,834 A | | 12/1999 | Wang et al. |
| 6,014,576 A | * | 1/2000 | Raley ........................... 600/344 |
| 6,061,584 A | * | 5/2000 | Lovejoy et al. ............. 600/344 |
| 6,256,523 B1 | | 7/2001 | Diab et al. |

FOREIGN PATENT DOCUMENTS

EP          0 313 238 A2    10/1988

OTHER PUBLICATIONS http://www.masimo.com/systemo.htm, "System Overview & Performance", 2 pages, reviewed on Sep. 17, 1999.
http://www.,masimo.com/pandt.htm, "Products & Technology", 1 page, reviewed on Sep. 17, 1999.
http://www.masimo.com/cables.htm, "Patient Cables", 1 page, reviewed on Sep. 17, 1999.
http://www.masimo.com/adt.htm, "Inop adt—Adult Disposable Digit Sensor", 1 page, reviewed on Sep. 17, 1999.
http://www.mrequipment.com/products/pulse_oximetry.htm, "MR Equipment Magnetic Resonance Equipment Corporation, Pulse Oximetry in MRI Model 3500 Pulse Oximeter", 2 pages, reviewed on Sep. 17, 1999.
http://www.mrequipment.com/products/oximetry_patient_mntrg.htm, "MR Equipment Magnetic Resonance Equipment Corporation, MR–Compatible High–Performance Optical Fiber Sensors, Pulse Oximetry Sensors for MRI Fiber Optic Sensors for use with MR–Compatible Pulse Oximeter", 2 pages, reviewed on Sep. 17, 1999.
Masimo Corporation, "Discrete Saturation Transform Example", reviewed on Sep. 17, 1999.

* cited by examiner

*Primary Examiner*—Eric F. Winakur
*Assistant Examiner*—Matthew Kremer
(74) *Attorney, Agent, or Firm*—Knobbe, Martens, Olson and Bear, LLP

(57) ABSTRACT

A pulse oximeter sensor has both a reusable and a disposable portion. The reusable portion of the sensor preserves the relatively long-lived and costly emitter, detector and connector components. The disposable portion of the sensor is the relatively inexpensive adhesive tape component that is used to secure the sensor to a measurement site, typically a patient's finger or toe. The disposable portion of the sensor is removably attached to the reusable portion in a manner that allows the disposable portion to be readily replaced when the adhesive is expended or the tape becomes soiled or excessively worn. The disposable portion may also contain an information element useful for sensor identification or for security purposes to insure patient safety. A conductive element that allows a pulse oximeter monitor to read the information element is located on the disposable portion in such a way that continuity is broken when the adhesive tape become torn, such as upon removal from the measurement site.

24 Claims, 11 Drawing Sheets

RESPOSABLE PULSE OXIMETRY SENSOR

BACKGROUND OF THE INVENTION

1. Field of the Invention

The present invention relates in general to sensors for measuring oxygen content in the blood, and, in particular, relates to resposable (reusable/disposable) sensors having an information element contained therein.

2. Background

Early detection of low blood oxygen is critical in a wide variety of medical applications. For example, when a patient receives an insufficient supply of oxygen in critical care and surgical applications, brain damage and death can result in just a matter of minutes. Because of this danger, the medical industry developed oximetry, a study and measurement of the oxygen status of blood. One particular type of oximetry, pulse oximetry, is a widely accepted noninvasive procedure for measuring the oxygen saturation level of arterial blood, an indicator of the oxygen status of the blood. A pulse oximeter relies on a sensor attached to a patient in order to measure the blood oxygen saturation.

Conventionally, a pulse oximeter sensor has a red emitter, an infrared emitter, and a photodiode detector. The sensor is typically attached to a patient's finger, earlobe, or foot. For a finger, the sensor is configured so that the emitters project light through the outer tissue of the finger and into the blood vessels and capillaries contained inside. The photodiode is positioned at the opposite side of the finger to detect the emitted light as it emerges from the outer tissues of the finger. The photodiode generates a signal based on the emitted light and relays that signal to an oximeter. The oximeter determines blood oxygen saturation by computing the differential absorption by the arterial blood of the two wavelengths (red and infrared) emitted by the sensor.

Conventional sensors are either disposable or reusable. A disposable sensor is typically attached to the patient with an adhesive wrap, providing a secure contact between the patient's skin and the sensor components. A reusable sensor is typically a clip that is easily attached and removed, or reusable circuitry that employs a disposable attachment mechanism, such as an adhesive tape or bandage. clip that is easily attached and removed, or reusable circuitry that employs a disposable attachment mechanism, such as an adhesive tape or bandage.

The disposable sensor has the advantage of superior performance due to conformance of the sensor to the skin and the rejection of ambient light. However, repeated removal and reattachment of the adhesive tape results in deterioration of the adhesive properties and tearing of the tape. Further, the tape eventually becomes soiled and is a potential source of cross-patient contamination. The disposable sensor must then be thrown away, wasting the long-lived emitters, photodiode and related circuitry.

On the other hand, the clip-type reusable sensor has the advantage of superior cost savings in that the reusable pulse sensor does not waste the long-lived and expensive sensor circuitry. However, as mentioned above, the clip-type reusable sensor does not conform as easily to differing patient skin shape, resulting in diminished sensitivity and increased ambient light.

Similar to the clip-type reusable sensor, the circuit-type reusable sensor advantageously does not waste the sensor circuitry. On the other hand, the circuit-type reusable sensor fails to provide quality control over the attachment mechanism. Much like the disposable sensors, the attachment mechanism for the circuit-type reusable sensor may become soiled or damaged, thereby leading to cross-patient contamination or improper attachment. Moreover, because the reusable circuit is severable from the attachment mechanism, operators are free to use attachment mechanisms that are either unsafe or improper with regard to a particular type of reusable circuitry.

Based on the foregoing, significant and costly drawbacks exist in conventional disposable and reusable oximetry sensors. Thus, a need exists for an oximetry sensor that incorporates the advantages found in the disposable and reusable sensors, without the respective disadvantages.

SUMMARY OF THE INVENTION

Accordingly, one aspect of the present invention is to provide a reusable/disposable (resposable) sensor having a disposable adhesive tape component that can be removed from other reusable sensor components. This hybrid sensor combines the longevity and associated cost advantages of the reusable sensor with the performance features of the disposable.

In one embodiment of the resposable sensor, the disposable tape includes an information element along with a mechanism for the electrical connection of the information element to the emitters. The information element provides an indication to an attached oximeter of various aspects of the sensor.

According to another embodiment, the information element provides an indication of the sensor type. According to yet another embodiment, the information element provides an indication of the operating characteristics of the sensor. In yet another embodiment, the information element provides security and quality control. For instance, the information element advantageously indicates that the sensor is from an authorized supplier.

According to yet another embodiment, the information element is advantageously located in the disposable portion and configured to be in communication with the reusable portion via a breakable conductor. The breakable conductor is also located within the disposable portion such that excessive wear of the disposable portion results in isolation of the information element, thereby indicating that the disposable portion should be replaced. Moreover, the information element may comprise one or more passive or active components, ranging from a single coding resistor to an active circuit, such as a transistor network, a memory device, or a central processing component.

Therefore, one aspect of the present invention is a pulse oximetry sensor including a reusable portion having an emitter configured to transmit light through tissue, a detector configured to receive light from tissue, a first contact, an external connector configured to attach to a monitor, and electrical circuitry configured to provide electrical communications to and from the external connector, the emitter, the detector and the first contact. The pulse oximetry sensor also includes a disposable portion configured to attach the reusable portion to the tissue. The disposable portion has an information element, a breakable conductor, and a second contact electrically connecting the information element and the breakable conductor, the second contact configured to create an electrical connection to the first contact when the disposable portion is combined with the reusable portion.

Another aspect of the present invention is a resposable sensor for noninvasively measuring a physiological parameter in tissue. The resposable sensor includes a reusable portion and a disposable portion. The disposable portion has at least one of an information element and a conductor electrically connected to the reusable portion. Moreover, the disposable portion is configured to secure the reusable portion to a measurement site.

Another aspect of the present invention is a method of providing disposable oximeter sensor elements. The method includes forming a disposable housing configured to receive a reusable electronic circuit. The method also includes forming at least one of an information element and a conductor associated with the disposable housing and configured to be disconnected from the reusable electronic circuit when the disposable housing is damaged, overused, or repeatedly attached.

Another aspect of the present invention is a method of providing reusable oximeter sensor elements. This includes forming a reusable electronic circuit configured to electrically connect with electronic components of a disposable housing and to employ the disposable housing for attachment to a measurement site.

Another aspect of the present invention is a method of measuring a tissue characteristic. This method includes creating a sensor through combining reusable electronic circuitry with a first disposable material such that an electrical connection is made between the reusable electronic circuitry and electronic components associated with the first disposable material. Moreover, the method includes attaching the sensor to a measurement site, removing the sensor, separating the reusable electronic circuitry from the first disposable material, and recombining the reusable electronic circuitry with a second disposable material.

Another aspect of the present invention is a pulse oximeter having a sensor including a reusable portion and a disposable portion. The disposable portion includes an information element electrically connected to the reusable portion through a breakable conductor. The breakable conductor is configured to electrically disconnect the information element from the reusable portion in the event of overuse, damage, or excessive reattachment of the disposable portion. Moreover, the pulse oximeter includes a monitor, and a cable for connecting the sensor to the monitor.

Yet another aspect of the present invention is a pulse oximeter sensor element having a disposable material that incorporates electronic components. The disposable material is configured to removably receive reusable oximeter sensor elements such that the electronic components electrically connect with the reusable oximeter sensor elements. Moreover, the disposable material is configured to secure the reusable oximeter sensor elements to a measurement site.

Another aspect of the present invention is a pulse oximeter sensor element including reusable electronic circuitry configured to electrically connect with electronic components of a disposable material and to employ the disposable material for attachment to a measurement site.

Another aspect of the present invention is a resposable sensor for measuring a tissue aspect. The resposable sensor includes a face tape, a base tape removably attached to the face tape, and reusable measurement circuitry removably secured between the face tape and the base tape. The reusable measurement circuitry is also configured to connect to an external monitor and configured to measure an aspect of tissue at a measurement site. Moreover, the face tape includes at least one of an information element and a breakable conductor connected to the reusable measurement circuitry when the reusable measurement circuitry is secured to the face tape.

Another aspect of the present invention is a resposable sensor having a reusable emitter and detector removably connected to a patient cable. The resposable sensor also includes a replaceable envelope having electronic circuitry configured to attach to the reusable emitter and detector such that the electronic circuitry monitors at least one characteristic of the resposable sensor. Moreover, the replaceable envelope is configured to removably receive the reusable emitter and detector and configured to secure the reusable emitter and detector to a measurement site.

Yet another aspect of the present invention is a pulse oximetry sensor having an emitter, a detector and a connector. The emitter is configured to transmit light through tissue and the detector is configured to receive light from tissue to measure a physiological parameter. Further, the connector is configured to provide electrical communications between the detector and emitter and a monitor. The pulse oximetry sensor includes a reusable portion having the emitter, the detector, the connector and a first contact in communication with the connector. Moreover, the sensor includes a disposable portion having a second contact, an information element and a conductive element disposed on an adhesive substrate configured to secure the reusable portion to a measurement site. The disposable portion removably attaches to the reusable portion in a first position such that the first contact contacts the second contact. The disposable portion detaches from the reusable portion in a second position. Also, the conductive element has a continuity condition connecting the information element to the second contact so that the information element is in communication with the connector. The conductive element has a discontinuity condition isolating the information element from the second contact and the connector. The discontinuity condition results from use of the disposable portion substantially beyond a predetermined amount.

DETAILED DESCRIPTION OF THE PREFERRED EMBODIMENT

The configuration of an information element for an oximeter sensor and method of reading an information element with an attached oximeter is described in U.S. Pat. No. 5,758,644, assigned to the assignee of the current application, and incorporated by reference herein. Accordingly, the configuration and the implementation of an information element will be greatly summarized as follows.

Figure 1:
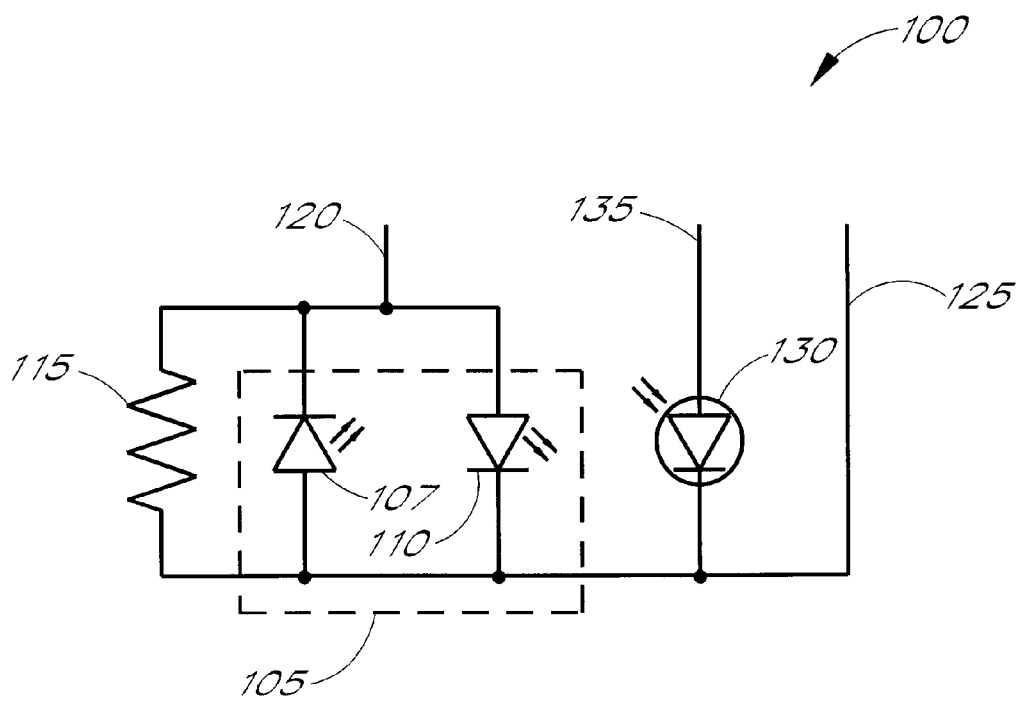
FIG. 1 illustrates a circuit diagram of a conventional disposable sensor having an information element.

FIG. 1 illustrates a conventional oximeter sensor circuit 100. The oximeter sensor circuit 100 includes an emitter 105 comprising a first LED 107 and a second LED 110. The oximeter sensor circuit further includes an information element comprising a resistor 115. The first LED 107, the second LED 110 and the resistor 115 are connected in parallel. The parallel connection has a common input electrical connection 120 and a common return 125. The oximeter sensor circuit 100 also includes a photodetector 130 having an input electrical connection 135 connected to one end and having the common return 125 connected to the other end.

As mentioned, the resistor 115 is provided as an information element that can be read by an attached oximeter. In order to read the resistor 115, the oximeter drives the oximeter sensor circuit 100 at a level where the emitter 105 draws effectively insignificant current. As is well understood in the art, the emitter 105 becomes active only if driven at a voltage above a threshold level. Thus, at this low level, significantly all of the current through the input electrical connection 120 flows through the resistor 115. By reducing the drive voltage across the input electrical connection 120 and common return 125 to a low enough level to not activate the emitter 105, the emitter 105 is effectively removed from the oximeter sensor circuit 100. Thus, the oximeter can determine the value of the resistor 115.

The value of the resistor 115 can be preselected to indicate, for example, the type of sensor (e.g., adult, pediatric, or neonatal), the operating wavelength, or other parameters about the sensor. The resistor 115 may also be utilized for security and quality control purposes. For example, the resistor 115 may be used to ensure that the oximeter sensor circuit 100 is configured properly for a given oximeter. For instance, the resistor 115 may be utilized to indicate that the oximeter sensor circuit 100 is from an authorized supplier.

An information element other than the resistor 115 may also be utilized. The information element need not be a passive device. Coding information may also be provided through an active circuit, such as a transistor network, memory chip, or other identification device.

Furthermore, it will be understood by a skilled artisan that a number of different circuit configurations can be implemented that allow the oximeter sensor circuit 100 to include an information element. For example, the emitter 105 and the information element may each have individual electrical connections.

As mentioned above, the resistor 115 is preselected such that at low drive voltages, it is the only circuit element sensed by the oximeter. On the other hand, the resistor 115 can also be preselected be of a sufficiently high value that when the drive voltage rises to a level sufficient to drive the emitter 105, the resistor 115 is effectively removed from the oximeter sensor circuit 100. Thus, the resistor 115 does not affect normal operations of the emitter 105. In summary, an information element may form an integral part of the oximeter sensor circuit 100 by providing valuable information to the attached oximeter.

Figure 2A:
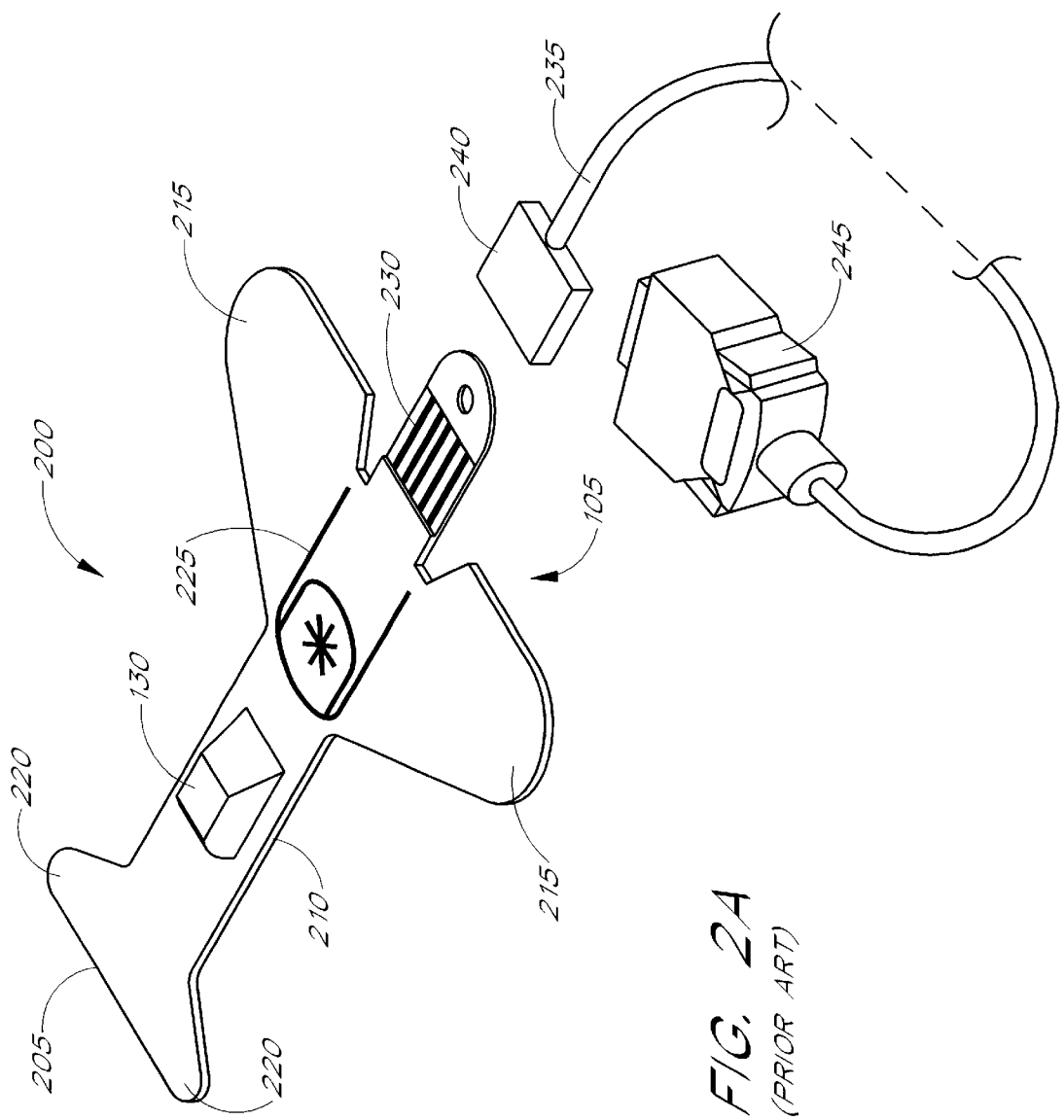
FIGS. 2A and 2B illustrate perspective views of the conventional disposable sensor.
Figure 2B:
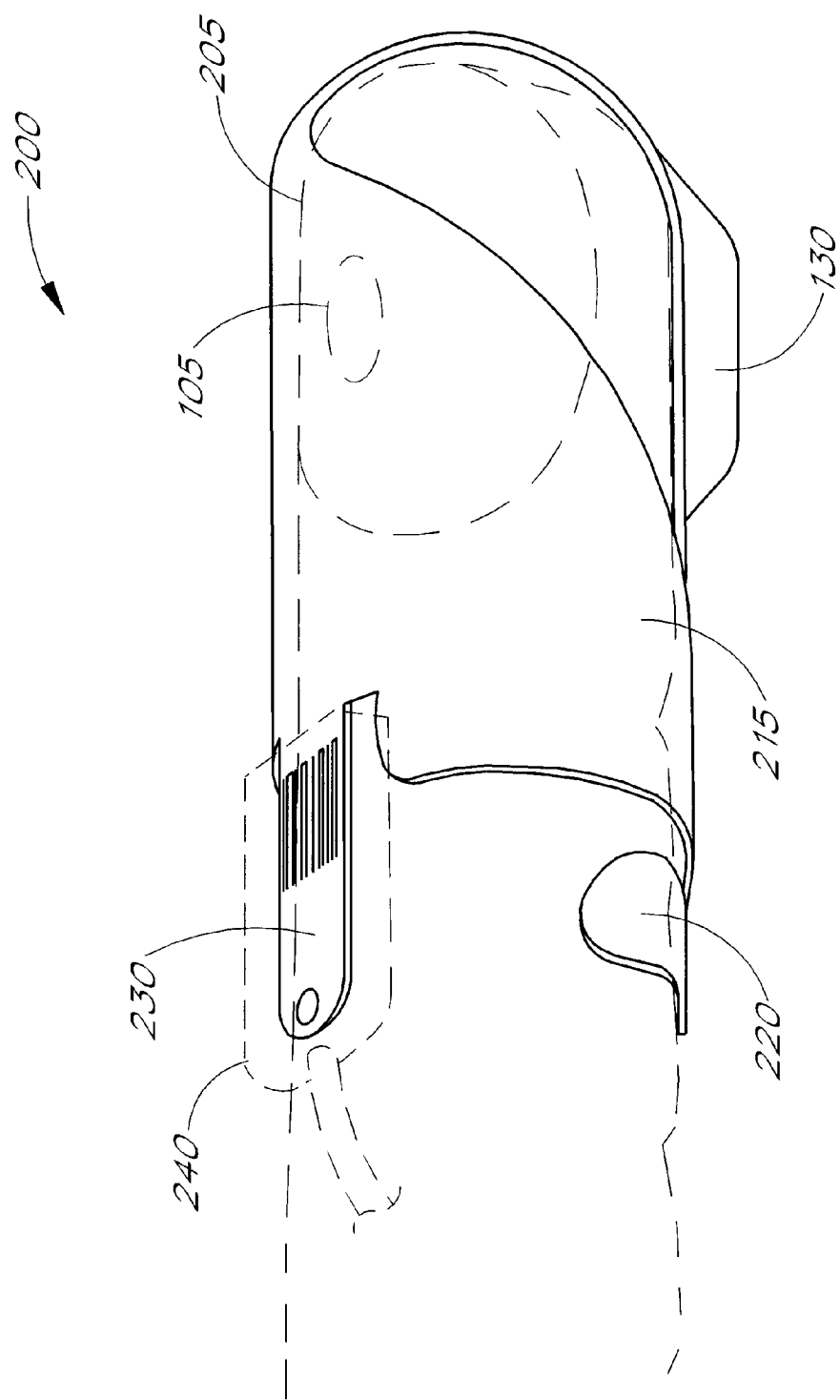

FIGS. 2A and 2B illustrate a conventional disposable sensor 200. The disposable sensor 200 includes an adhesive substrate 205 having an elongated center portion 210 with front and rear flaps, 215 and 220, extending outward from the elongated center portion 210. The adhesive substrate 205 may also have an image 225 superimposed on the adhesive substrate 205 so as to indicate proper use.

The elongated center portion 210 includes the oximeter sensor circuit 100 of FIG. 1. For example, the emitter 105 is housed on an underside of the elongated center portion 210 approximately beneath the superimposed image 225. Thus, as shown in FIG. 2A, the emitter 105 may be housed approximately beneath the asterisk superimposed on the image of a fingernail. On the other hand, the photodetector 130 is housed on the topside of the elongated center portion 210 in proximity with the rear flaps 220.

The elongated center portion 210 further includes an electrical connector 230 to drive the emitter 105 and to receive an output from the photodetector 130. The electrical connector 230 is preferably configured to attach to a connector cable 235 via a sensor connector 240. Also, the connector cable 235 attaches to or connects with an oximeter via an oximeter connector 245.

FIG. 2B illustrates an example of how the disposable sensor 200 wraps the front and rear flaps 215 and 220 around a finger such that the adhesive substrate 205 provides a secure contact between the patient's skin, the emitter 105 and the photodetector 130. FIG. 2B also illustrates an example of the sensor connector 240 (shown in broken lines) encompassing the electrical connector 230.

As shown in FIGS. 1–2B, the conventional disposable sensor 200 integrates the components of the conventional oximeter sensor circuit 100 such that disposal of the disposable sensor 200 includes disposal of the longer lasting, expensive circuitry found therein.

Figure 3:
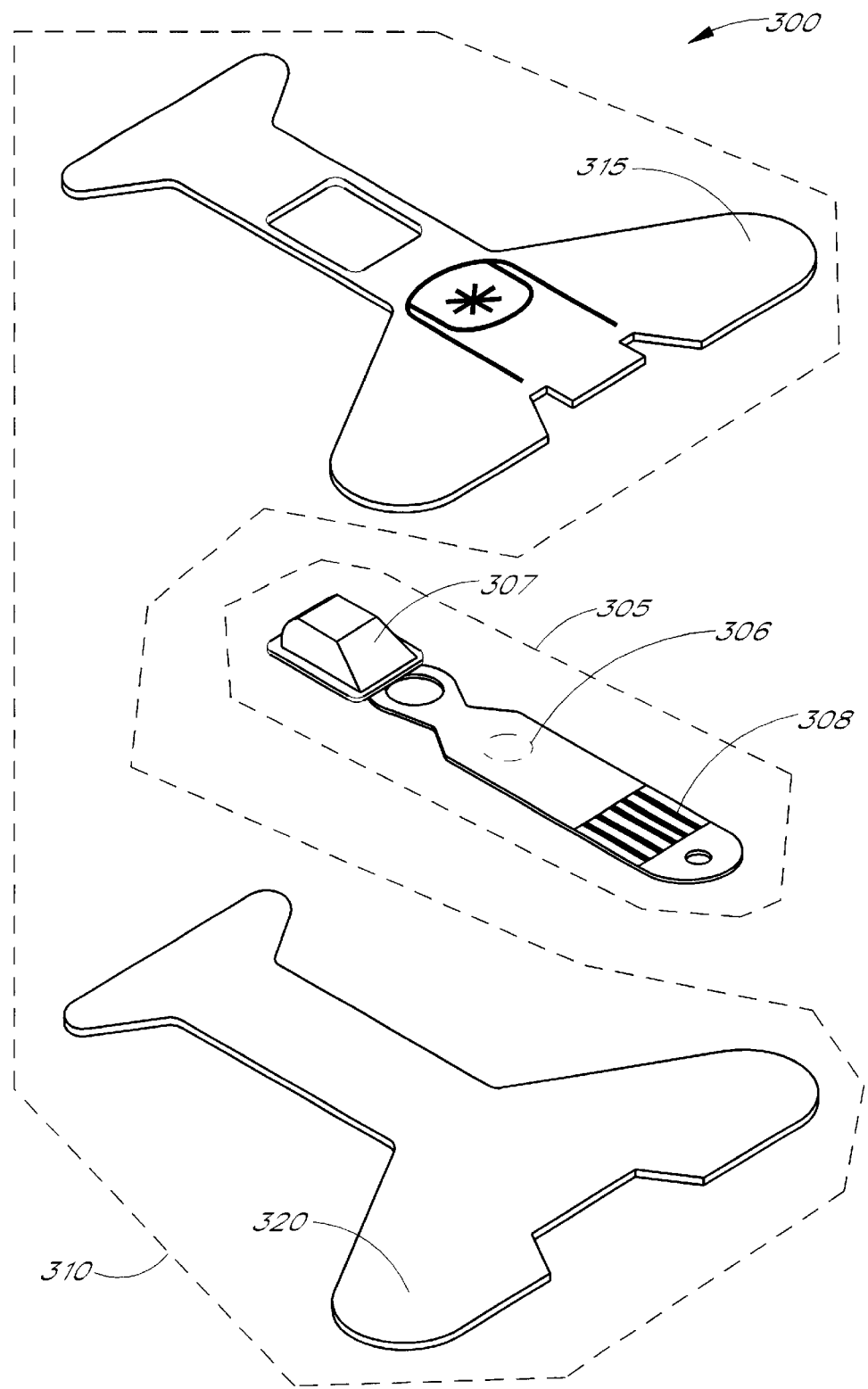
FIG. 3 illustrates an exploded view of a resposable sensor having two disposable tape layers, according to one embodiment of the invention.

FIG. 3 illustrates an exploded view of one embodiment of a resposable (reusable/disposable) sensor 300 according to the present invention. In this embodiment, the resposable sensor 300 includes a reusable portion 305 having an emitter 306, a photodetector 307 and an electrical connector 308. The resposable sensor also includes a disposable portion 310 having a face tape layer 315 and a clear base tape layer 320. As shown in FIG. 3, the disposable portion 310 attaches to the reusable portion 305 by sandwiching the reusable portion 305 between a face tape layer 315 and a clear base tape layer 320.

According to this embodiment, conventional adhesives or other attaching methodology may be used to removably attach the face tape layer 315 to the clear base tape layer 320. Furthermore, the adhesive properties associated with the base of the conventional disposable sensor 200 may be the same as the adhesive properties on the base of the clear base tape layer 320, as both portions are provided to attach to the patient's skin.

As mentioned, the disposable portion 310 removably attaches to the reusable portion 305 in, for example, a sandwich or layered style. After removably attaching the disposable portion 310 to the reusable portion 305, the resposable sensor 300 functions similar to the disposable sensor 200, i.e., the resposable sensor 300 wraps flaps around a patient's tissue such that the emitter 306 and the photodetector 307 align on opposite sides of the tissue. However, in contrast to the disposable sensor 200, the resposable sensor 300 provides for reuse of the reusable portion 305. For example, when the disposable portion 310 becomes contaminated, worn, or defective, rather than discarding the entire resposable sensor 300, the disposable portion 310 is removed such that the reusable portion 305 may be re-removably attached to a new disposable portion 310. The discarding of the disposable portion 310 completely avoids cross-contamination through the reuse of adhesive tapes between patients without wasting the more costly and longer lasting sensor circuitry of the resposable portion 305. Note that optional sterilization procedures may be advantageously performed on the reusable portion 305 before reattachment to either the new disposable portion 310 or to the patient, in order to further ensure patient safety.

Figure 4:
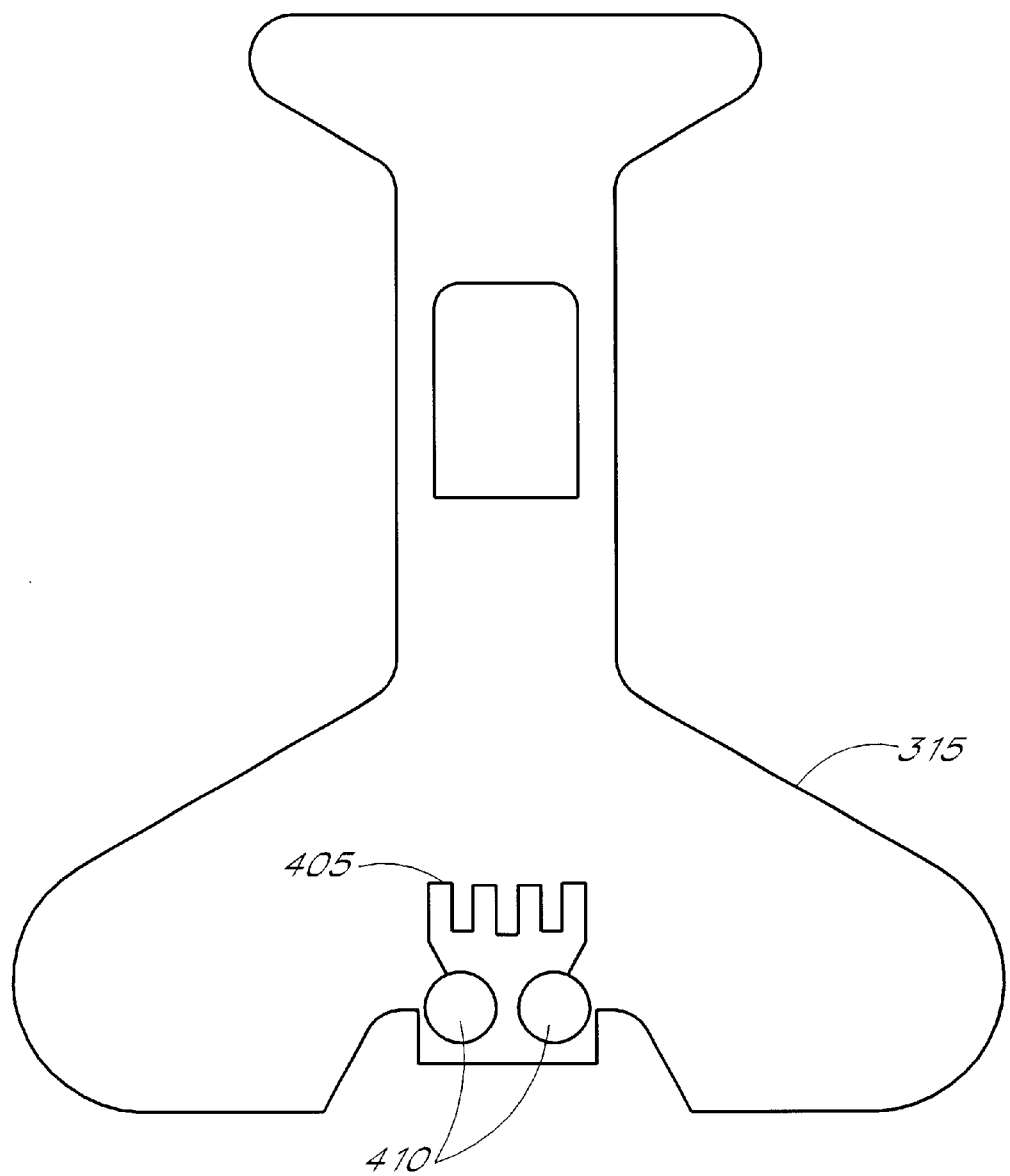
FIG. 4 illustrates a top view of one of the disposable tape layers of FIG. 3 incorporating an information element.

FIG. 4 illustrates a top view of an embodiment of the face tape layer 315 of the disposable portion 310 of the resposable sensor 300. According to this embodiment, the face tape layer 315 further includes an information element 405 as an integral part of the face tape layer 315. In this embodiment, the information element 405 is a resistive element made by depositing a conductive ink trace having a predetermined length and width. As is known in the art, the length, width and conductivity of the conductive ink trace determines the resistance of the resistive element. The information element 405 is deposited between contacts 410 that are also implemented with conductive ink. It will be understood by a skilled artisan that a variety of methods can be used for mating the contacts 410 with the electrical circuitry of the reusable portion 305. For example, the contacts 410 may advantageously physically touch the leads or the electrical connector 308 such that the reusable portion 305 is electrically configured to include the information element 405. Such a configuration employs the oximeter sensor circuit 100 of FIG. 1, having elements thereof distributed in both the reusable portion 305 and the disposable portion 310 of the resposable sensor 300.

In the foregoing embodiment, the disposable portion 310 comprises the information element 405 along with the face tape layer 315 and the clear base layer 320. As mentioned, the disposable portion 310 is removably attached to the reusable portion 305 and is employed in a similar manner as the disposable sensor 200. In contrast to the disposable sensor 200, when the disposable portion 310 of the resposable sensor 300 becomes worn, the disposable portion 310 and the information element 405 are discarded and the reusable portion 305 is saved. By discarding the information element, the attached oximeter can perform quality control. For example, if the reusable portion 305 is reattached to a patient using either a simple adhesive or any other non-authorized disposable mechanism, the resposable sensor 300 will not include the information element 405. As mentioned above, an attached oximeter can recognize the absence of the information element 405 and create an appropriate response indicating inappropriate use of the reusable portion 305 of the resposable sensor 300.

Figure 5:
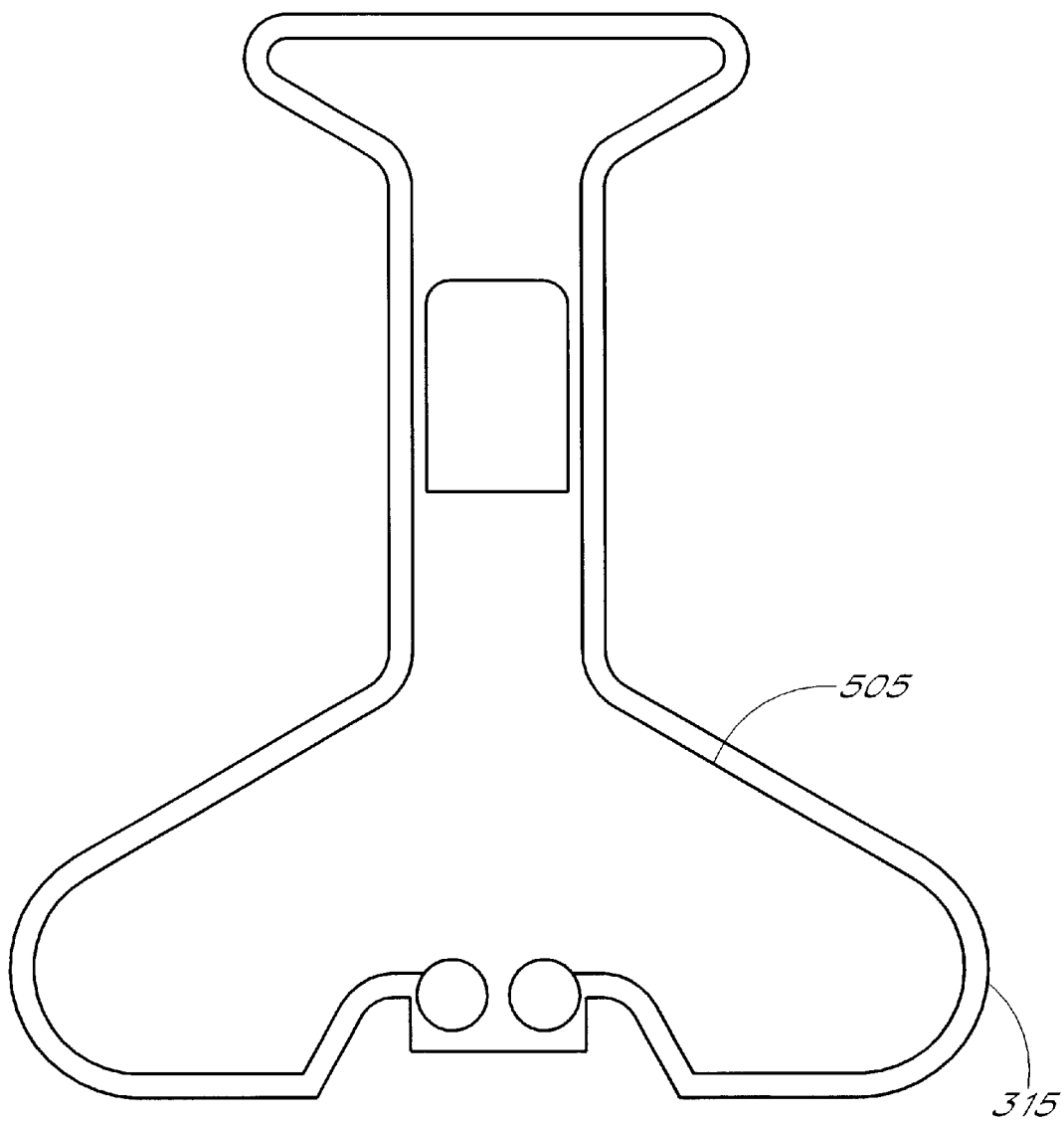
FIG. 5 illustrates a top view of one of the disposable tape layers of FIG. 3 incorporating a breakable conductor.
Figure 6A:
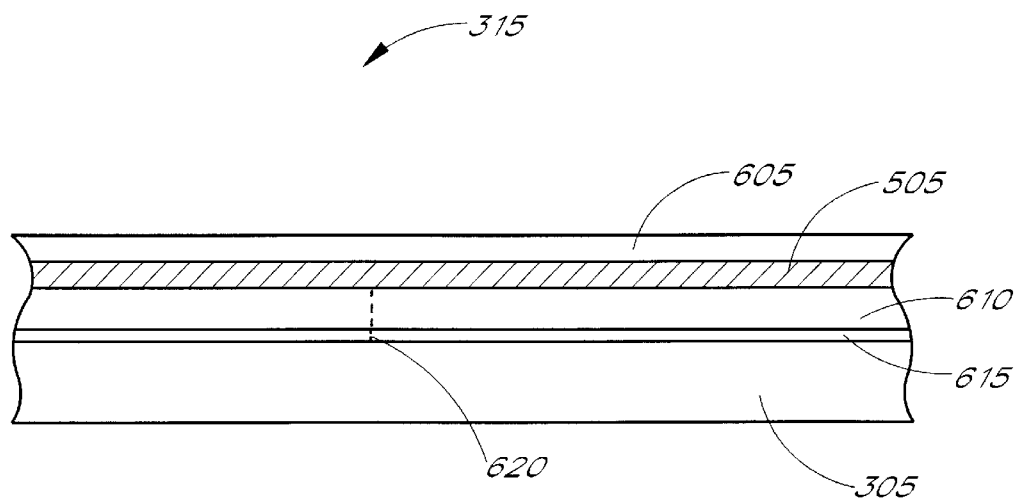
FIGS. 6A and 6B illustrate cross-sectional views of a portion of the disposable tape layer of FIG. 5.
Figure 6B:
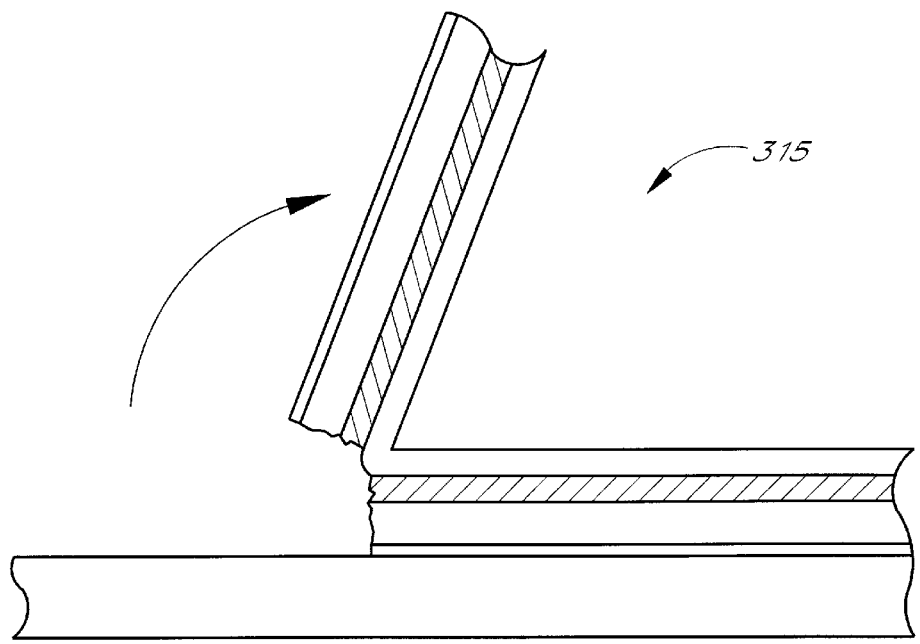

FIG. 5 illustrates a top view of yet another embodiment of the face tape layer 315 of the disposable portion 310 of the resposable sensor 300. In this embodiment, the face tape layer 315 includes a breakable conductor 505 comprising a conductive ink trace located approximately along the periphery of the face tape layer 315. This location ensures that a tear along the periphery of the face tape layer 315 results in a tear, or electrical discontinuity, in the breakable conductor 505. For example, FIGS. 6A and 6B illustrate the face tape layer 315 in which the breakable conductor 505 is layered between a tape stock 605 and a tape base 610. The reusable portion 305 of the resposable sensor 300 then attaches to the tape base 610 through a pressure sensitive adhesive (PSA) 615. The PSA 615, the conductor 505 and the tape base 610 include a score 620 such that multiple attachment and removal of the resposable sensor 300 will result in a peripheral tear, or electrical discontinuity, in the breakable conductor 505, as illustrated in FIG. 6B.

Thus, like the information element 405, the breakable conductor 505 also provides security and quality control functions. In particular, repeated use of the disposable portion 305 of the resposable sensor 300 advantageously severs at least one part of the breakable conductor 505. An attached oximeter can detect such severance and initiate an appropriate notification to, for example, monitoring medical personnel. Providing security and quality control through a breakable conductor advantageously assists in controlling problems with patient contamination or improper attachment due to weakened adhesives.

Figure 7:
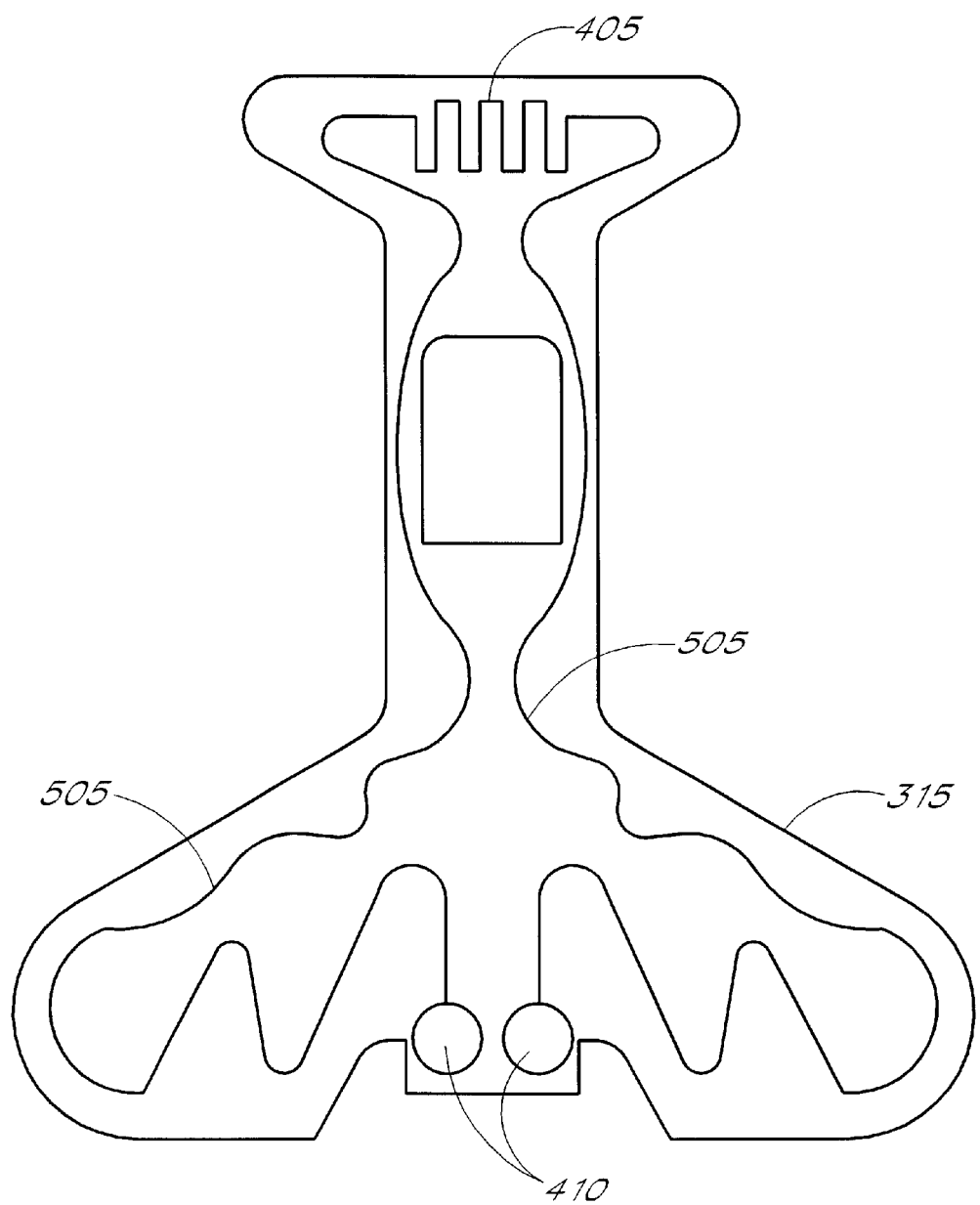
FIG. 7 illustrates a top view of one of the disposable tape layers of FIG. 3 incorporating the information element with a breakable conductor.

FIG. 7 illustrates yet another embodiment of the face tape layer 315. In this embodiment, the face tape layer 315 combines the breakable conductor 505 and the information element 405. In this embodiment, the breakable conductor 505 is printed in a serpentine pattern to further increase the probability of a discontinuity upon the tearing of any portion of the face tape layer 315. This combination of the information element 405 and the breakable conductor 505 advantageously adds significant safety features. For example, in this embodiment, the information element 405 is connected serially with the breakable conductor 505 and in parallel with the emitter 306 of the reusable portion 305. Therefore, any discontinuity or tear in the breakable conductor 505 separates the information element 405 from the circuitry of the reusable portion 305.

According to the foregoing embodiment, the attached oximeter receives an indication of both overuse and misuse of the resposable sensor 300. For example, overuse is detected through the tearing and breaking of the breakable conductor 505, thereby removing the information element 405 from the resposable sensor 300 circuitry. In addition, misuse through employment of disposable portions 310 from unauthorized vendors is detected through the absence of the information element 405. Moreover, misuse from purposeful shorting of the contacts 410 is detected by effectively removing the emitter 306 from the circuit, thereby rendering the resposable sensor 300 inoperative. Therefore, the resposable sensor 300 of this embodiment advantageously provides a multitude of problem indicators to the attached oximeter. By doing so, the resposable sensor 300 advantageously prevents the likelihood of contamination, adhesive failure, and misuse. The resposable sensor 300 also advantageously maintains the likelihood of quality control.

A skilled artisan will recognize that the concepts of FIGS. 3–7 may be combined in total or in part in a wide variety of devices. For example, either or both of the breakable conductor 505 and the information element 405 may advantageously be traced into the clear base tape layer 320 rather than into the face tape layer 315.

Figure 8A:
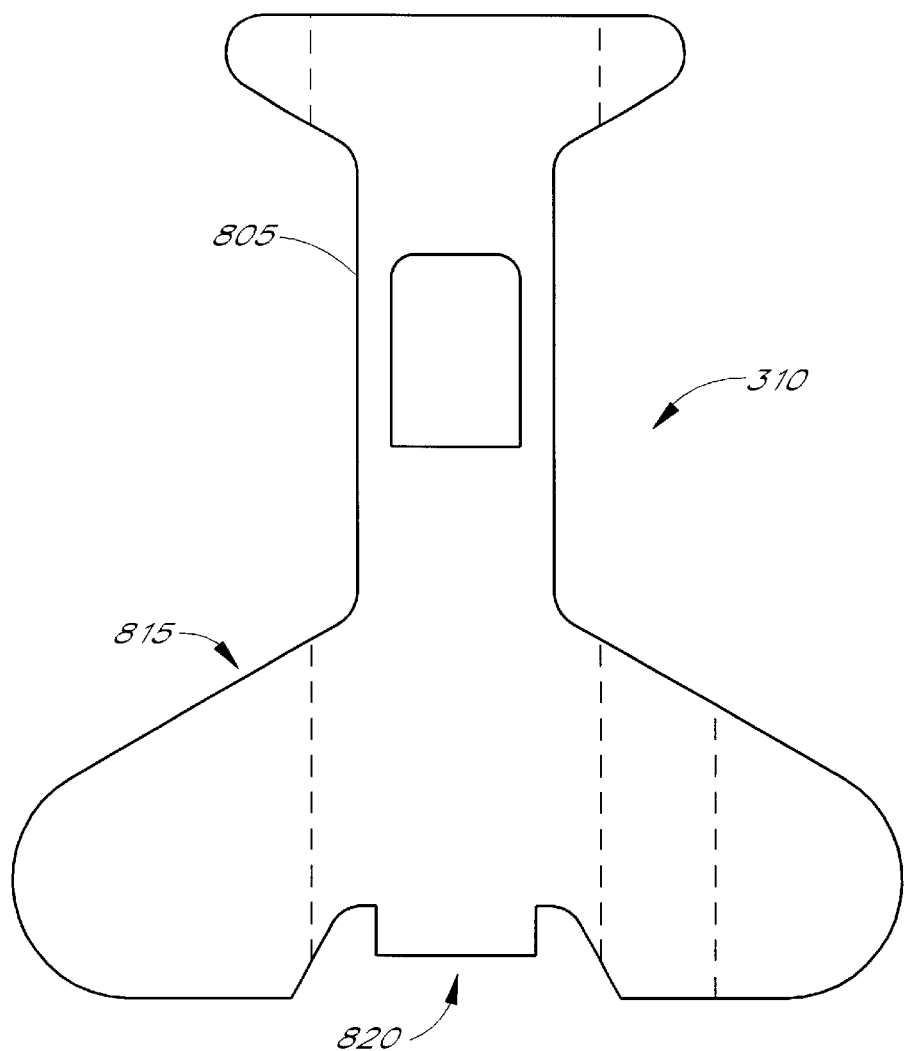
FIGS. 8A and 8B illustrate a top view and a side view, respectively, of one of the disposable layers of FIG. 3 configured as a fold-over tape.
Figure 8B:
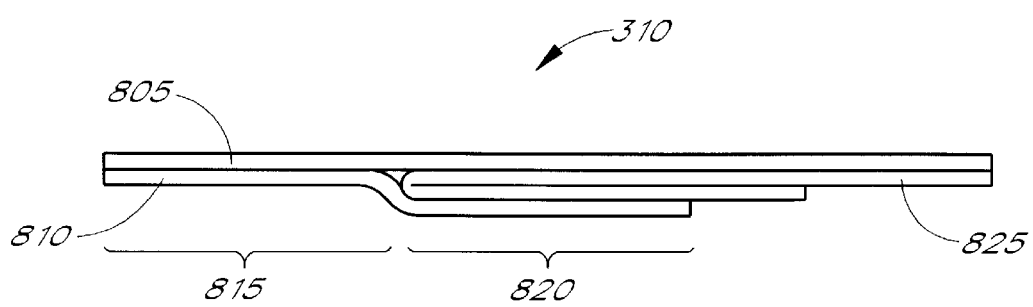

FIGS. 8A and 8B illustrate yet another embodiment of the disposable portion 310 of the resposable sensor 300 according to the present invention. As shown in this embodiment, the disposable portion 310 includes a face tape layer 805 and a clear base tape layer 810. According to this embodiment, the clear base tape layer 810 includes a preattached section 815 and a fold over section 820. The preattached section 815 attaches approximately one third of the face tape layer 805 to the clear base tape layer 810. On the other hand, the fold over section 820 forms a flap configured to create a cavity between the face tape layer 805 and the clear base tape layer 810. The cavity is configured to receive the reusable portion 305 of the resposable sensor 300. According to one embodiment, a release liner 825 fills the cavity and separates the face tape layer 805 from the clear base tape layer 810. When the release liner 825 is removed, newly exposed adhesive on the fold over section 820 and the face tape layer 805 removably attaches the reusable portion 305 between the face tape layer 805 and fold over section 820 of the clear base tape layer 810.

According to another embodiment, the cavity is so formed that adhesive is not needed. For example, the fold over section 820 may comprise resilient material that can form a friction fit relationship so as to fix the reusable portion 305 in an appropriate position relative to the disposable portion 310. On the other hand, the fold over section 820 may also comprise material having other than resilient or adhesive properties, but still allow for proper placement of the reusable portion 305 and disposable portion 310 on the patient. For example, hook-and-loop type materials like VELCRO® may be used.

It will be understood that a skilled artisan would recognize that the fold over embodiment of the responsible sensor 300 may employ the properties discussed in relation to FIGS. 3–7, such as the information element 405 and the breakable wire 505.

Figure 9A:
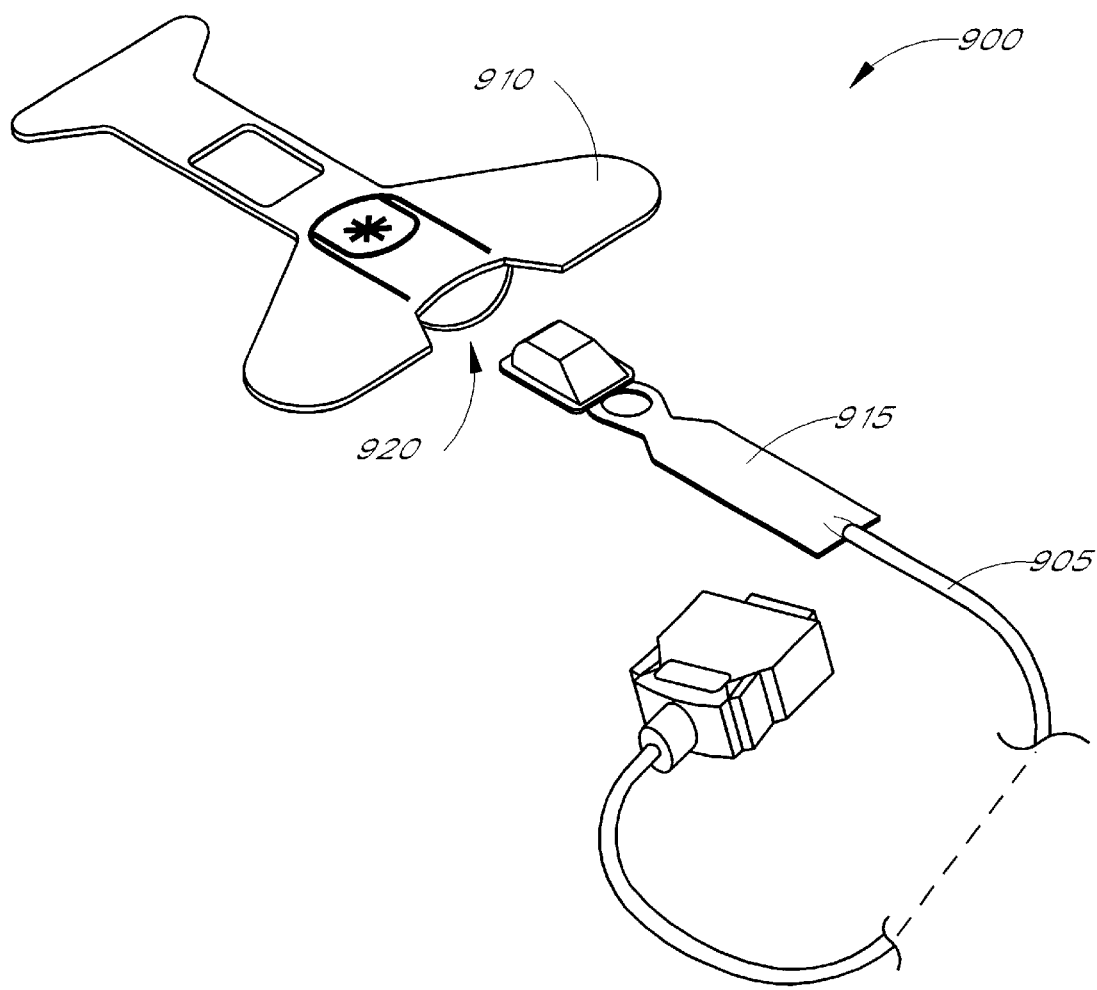
FIG. 9A illustrates a perspective view of a resposable sensor having a disposable portion configured as a tape sleeve and a reusable portion directly attached to a patient cable, according to another embodiment of the invention.

FIG. 9A illustrates an embodiment of a resposable sensor 900 integrated with an attached patient cable 905, according to another embodiment of the invention. In this embodiment, a disposable portion 910 is attached to a reusable portion 915 by removably inserting the reusable portion 915 into a tape envelope 920 formed in the disposable portion 910.

A skilled artisan will recognize that the disposable portion 910 may include the information element 405, the breakable wire 505, or both. Inclusion of one or both of these electronic components in the resposable sensor 900 advantageously provides the security, quality control, and safety features described in the foregoing embodiments.

Figure 9B:
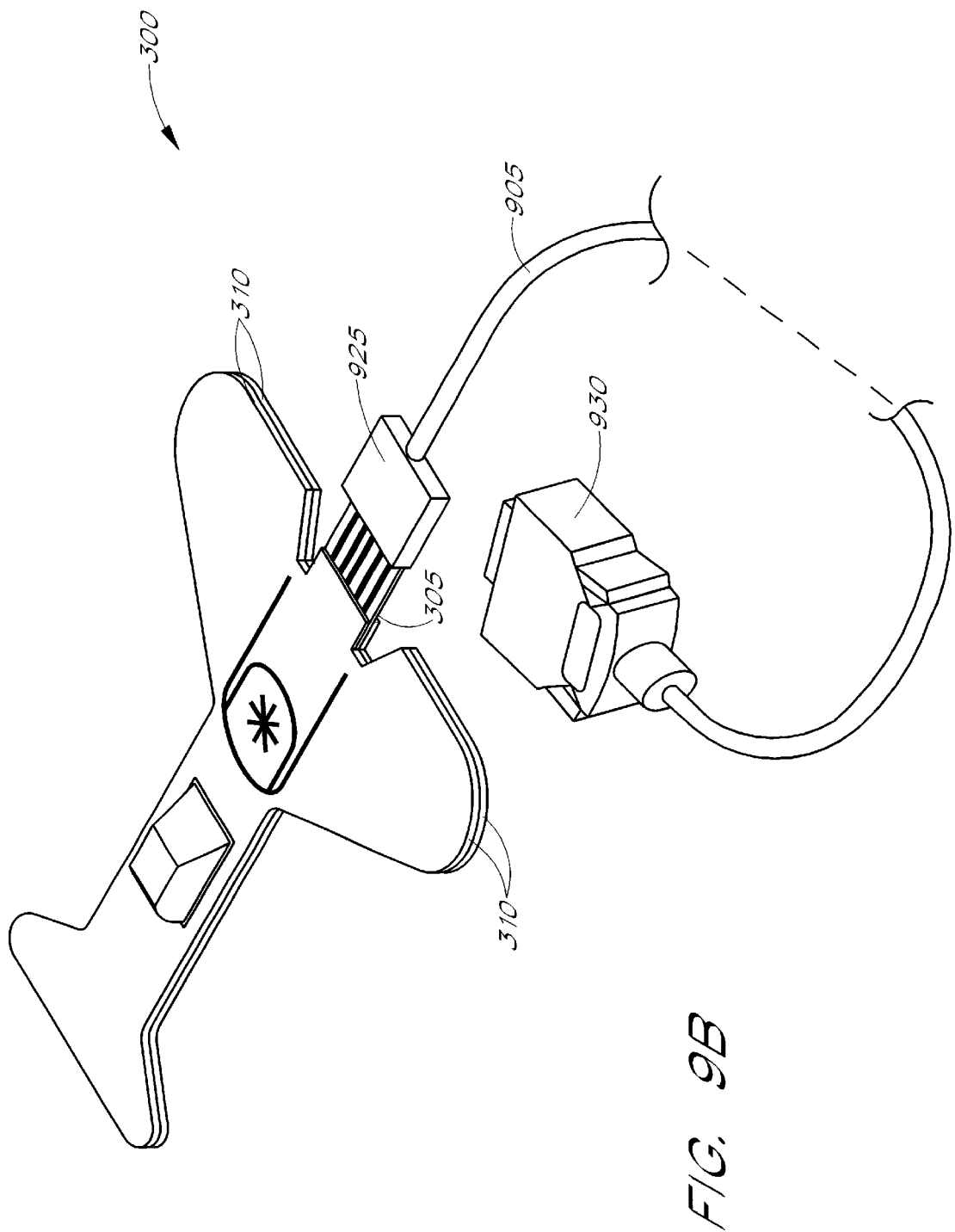
FIG. 9B illustrates a perspective view of a resposable sensor having a reusable portion removably attached to a patient cable, according to another embodiment of the invention.

FIG. 9B illustrates an embodiment of a resposable sensor 300 of FIG. 3, according to another embodiment of the invention. According to this embodiment, the resposable sensor 300 removably attaches to the patient cable 905 via a sensor connector 925. The patient cable 905 then attaches to an oximeter via an oximeter connector 930. Use of the sensor connector 925 enables the replacement of both the reusable portion 305 of the resposable sensor 300 without replacement of the sensor connector 925 or patient cable 905. In such an embodiment, the disposable portion 310 would follow a different, more frequent, replacement schedule than that of the reusable portion 305.

A skilled artisan will recognize that the variety of configurations described above that include the information element 405, the breakable wire 505, or both, may be incorporated into the embodiment of FIG. 9B.

Although the foregoing invention has been described in terms of certain preferred embodiments, other embodiments will be apparent to those of ordinary skill in the art. For example, select aspects of FIGS. 3–9B may be combined. For example, the envelope configured disposable portion 910 of FIG. 9A may be combined with the reusable portion 305 of FIG. 3.

Additionally, other combinations, omissions, substitutions and modifications will be apparent to the skilled artisan in view of the disclosure herein. Accordingly, the present invention is not intended to be limited by the reaction of the preferred embodiments, but is to be defined by reference to the appended claims.

What is claimed is:

1. A pulse oximetry sensor comprising:
   a reusable portion comprising
      an emitter configured to transmit light through tissue,
      a detector configured to receive light from tissue,
      a first contact,
      an external connector configured to attach to a monitor, and
      electrical circuitry configured to provide electrical communications to and
   from the external connector, the emitter, the detector and the first contact; and
   a disposable portion configured to attach the reusable portion to the tissue, the disposable portion comprising
      an information element;
      a breakable conductor, and
      a second contact electrically connecting the information element and the breakable conductor, the second contact configured to create an electrical connection to the first contact when the disposable portion is combined with the reusable portion.

2. A resposable sensor for noninvasively measuring a physiological parameter in tissue, the resposable sensor comprising:
   a reusable portion comprising an emitter and a detector; and
   a disposable portion comprising at least one of an information element and a conductor electrically connected to the reusable portion, wherein the disposable portion is configured to secure the reusable portion to a measurement site.

3. The resposable sensor according to claim 2, wherein the disposable portion is removably attached to the reusable portion with adhesive.

4. A method of providing disposable oximeter sensor elements, the method comprising:
   forming a disposable housing configured to receive a reusable electronic circuit; and
   forming a conductor trace within the disposable housing, the conductor trace configured to cause an electrical disconnect when the disposable housing is damaged, overused, or repeatedly attached.

5. A method of providing reusable oximeter sensor elements, the method comprising forming a reusable electronic circuit comprising an emitter and a detector, the reusable electronic circuit being configured to electrically connect with electronic components of a disposable housing and to employ the disposable housing for attachment to a measurement site.

6. A method of reusing costly circuitry of a sensor while reducing patient cross-contamination, the method comprising:
   creating a sensor through combining reusable electronic circuitry comprising an emitter and a detector, with a first disposable material such that an electrical connection is made between the reusable electronic circuitry and electronic components associated with the first disposable material;
   attaching the sensor to a measurement site;
   removing the sensor;
   separating the reusable electronic circuitry from the first disposable material; and
   recombining the reusable electronic circuitry with a second disposable material.

7. The method according to claim 6, wherein the step of creating a sensor includes electrically connecting a conductor employed in the first disposable material to the reusable electronic circuitry, wherein the conductor is configured to break upon overuse of the first disposable material.

8. A pulse oximeter comprising:
   a sensor comprising
      a reusable portion, and
      a disposable portion including a breakable conductor electrically connected to the reusable portion, the breakable conductor configured to cause an electrical disconnect in the event of overuse, damage, or excessive reattachment of the disposable portion;

a monitor; and a cable for connecting the sensor to the monitor.

9. The pulse oximeter according to claim 8, wherein the disposable portion comprises a removable layered structure comprising at least one layer above the reusable portion and one layer below the reusable portion before application of the sensor to a measurement site, such that the removable layered structure is configured to secure the sensor to the measurement site.

10. The pulse oximeter according to claim 8, wherein the disposable portion comprises an envelope configured to receive the reusable portion before application of the sensor to a measurement site, and wherein the disposable portion is configured to secure the sensor to the measurement site.

11. The pulse oximeter according to claim 8, wherein the disposable portion comprises a folded portion configured to receive the reusable portion before application of the sensor to a measurement site, and wherein the folded portion is configured to secure the sensor to the measurement site.

12. A pulse oximeter comprising:

a sensor comprising
  a reusable portion, and
  a disposable portion including an information element electrically connected to the reusable portion through a breakable conductor, the breakable conductor configured to electrically disconnect the information element from the reusable portion in the event of overuse, damage, or excessive reattachment of the disposable portion;

a monitor; and a cable for connecting the sensor to the monitor, wherein the reusable portion further comprises an emitter and a detector.

13. A pulse oximeter sensor element comprising a disposable material incorporating electronic components, wherein the disposable material is configured to removably receive reusable oximeter sensor elements comprising an emitter and a detector, such that the electronic components electrically connect with the reusable oximeter sensor elements, and wherein the disposable material is configured to secure the reusable oximeter sensor elements to a measurement site.

14. The pulse oximeter sensor element according to claim 13, wherein the electronic components include a breakable conductor.

15. A pulse oximeter sensor element comprising reusable electronic circuitry comprising an emitter and a detector, wherein the reusable electronic circuitry is configured to electrically connect with electronic components of a disposable housing and to employ the disposable material for attachment to a measurement site.

16. A resposable sensor for measuring a tissue aspect, the resposable sensor comprising:

a face tape;

a base tape removably attached to the face tape; and reusable measurement circuitry including at least one emitter and a detector, wherein the reusable measurement circuitry is removably secured between the face tape and the base tape, is configured to connect to an external monitor, and is configured to measure an aspect of tissue at a measurement site, wherein the face tape further includes at least one of an information element and a breakable conductor connected to the reusable measurement circuitry when the reusable measurement circuitry is secured to the face tape.

17. The resposable sensor according to claim 16, wherein the conductor traces the periphery of the face tape such that a discontinuity in the face tape isolates the information element from the reusable measurement circuitry.

18. The resposable sensor according to claim 16, wherein the information element comprises at least one of a resistor, a transistor network, a memory device, and a central processing unit.

19. A resposable sensor comprising:

a reusable emitter and detector removably connected to a patient cable, and a replaceable envelope comprising electronic circuitry configured to attach to the reusable emitter and detector such that the electronic circuitry monitors at least one characteristic of the resposable sensor, wherein the replaceable envelope is also configured to removably receive the reusable emitter and detector and configured to secure the reusable emitter and detector to a measurement site.

20. A pulse oximetry sensor comprising:

a reusable portion comprising
  an emitter,
  a detector,
  a connector configured to provide communication between the detector and a monitor and the emitter and the monitor, and
  a first contact in communication with the connector; and a disposable portion comprising
  a second contact, and
  an information element and a conductive element disposed on an adhesive substrate configured to secure the reusable portion to a measurement site, the disposable portion removably attached to the reusable portion in a first position such that the first contact contacts the second contact, and detached from the reusable portion in a second position, the conductive element comprising a continuity condition connecting the information element to the second contact so that the information element is in communications with the connector and a discontinuity condition isolating the information element from the second contact and the connector, the discontinuity condition resulting form use of the disposable portion substantially beyond a predetermined amount.

21. The method of claim 4, wherein the disposable housing further comprises a cavity configured to receive the reusable electronic circuit before application of the disposable housing to a measurement site.

22. The method of claim 21, wherein the cavity is at least partially formed by a fold over portion initially covered by release liner, thereby protecting the cavity until the reusable electronic circuit is received therein.

23. The method of claim 4, wherein the disposable housing further comprises an envelope configured to receive the reusable electronic circuit before application of the disposable housing to a measurement site.

24. The method of claim 5, wherein the electronic components comprise a breakable conductor which causes an open circuit when the breakable conductor is broken.

* * * * *

UNITED STATES PATENT AND TRADEMARK OFFICE
CERTIFICATE OF CORRECTION

PATENT NO. : 6,377,829 B1
DATED : April 23, 2002
INVENTOR(S) : Ammar Al-Ali

It is certified that error appears in the above-identified patent and that said Letters Patent is hereby corrected as shown below:

Column 12,
Line 48, please delete "form" and insert thereof, -- from --.

Signed and Sealed this

Sixth Day of December, 2005

JON W. DUDAS
*Director of the United States Patent and Trademark Office*